United States Patent [19]

Asato

[11] 4,154,740

[45] May 15, 1979

[54] SUBSTITUTED TETRAHYDROBENZOTHIOPHENES AND METHOD OF PREPARATION THEREOF

[75] Inventor: Goro Asato, Titusville, N.J.

[73] Assignee: American Cyanamid Company, Stamford, Conn.

[21] Appl. No.: 912,808

[22] Filed: Jun. 5, 1978

Related U.S. Application Data

[63] Continuation of Ser. No. 702,797, Jul. 6, 1976, abandoned, which is a continuation-in-part of Ser. No. 532,449, Dec. 13, 1974, abandoned, which is a continuation-in-part of Ser. No. 436,827, Jan. 25, 1974, abandoned.

[51] Int. Cl.$^2$ .................. C07D 333/16; A01N 9/00
[52] U.S. Cl. .................. 260/332.3 P; 260/329 F; 260/329 S; 260/329 HS; 260/329 AM; 260/332.2 A; 260/332.3 C; 260/332.5; 424/275; 426/648
[58] Field of Search ......... 260/329 HS, 329 F, 329 S, 260/329 AM, 332.3 P, 332.5, 332.2 A, 332.3 C

[56] References Cited

U.S. PATENT DOCUMENTS 3,998,959  12/1976  Asato et al. .................. 260/332.2 R

*Primary Examiner*—A. Siegel
*Attorney, Agent, or Firm*—Harry H. Kline

[57] ABSTRACT

This disclosure describes novel 4,5,6,7-tetrahydrobenzo[b]thien-7-ylureas useful as herbicidal agents and animal growth regulants and processes for the preparation thereof.

25 Claims, No Drawings

SUBSTITUTED TETRAHYDROBENZOTHIOPHENES AND METHOD OF PREPARATION THEREOF

CROSS REFERENCE TO RELATED APPLICATIONS

This application is a continuation of my copending application, Ser. No. 702,797, filed on July 6, 1976 now abandoned, which is a continuation-in-part of my abandoned application Ser. No. 532,449, filed Dec. 13, 1974, which in turn is a continuation-in-part of my abandoned application Ser. No. 436,827, filed Jan. 25, 1974

BRIEF SUMMARY OF THE INVENTION

This invention relates to novel 4,5,6,7-tetrahydrobenzo[b]thien-7-ylureas which may be represented by the following general formula:

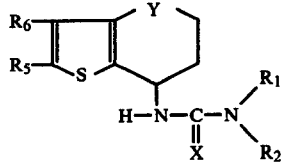

wherein X is a divalent oxygen or divalent sulfur; Y is a divalent moiety of the formulae:

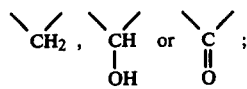

$R_1$ is hydrogen, alkyl $C_1$–$C_4$, cycloalkyl $C_3$–$C_6$, allyl, 2-propynyl, benzyl or β-phenylethyl; $R_2$ is selected from the group consisting of the substituents listed in Table I below:

TABLE I

| $R_2$ |
|---|
| hydrogen |
| alkyl $C_1$–$C_{12}$ |
| cycloalkyl $C_3$–$C_6$ |
| allyl |
| methallyl |
| 2-butenyl |
| 2-propynyl |
| hydroxy |
| alkoxy $C_1$–$C_6$ |
| allyloxy |
| methallyloxy |
| 2-butenyloxy |
| methoxymethyl |
| —O—CH$_2$—COOH |
| phenoxy |
| benzyloxy |
| —CH$_2$—CH$_2$—OH |
| —CH$_2$—CH$_2$—O—CH$_3$ |
| —CH$_2$—CH$_2$—S—CH$_3$ |
| —CH$_2$—CH(OR)$_2$ |
| —CH$_2$—CF$_3$ |
| —CH$_2$—CN |
| —CH$_2$—CO$_2$R |
| —NH—CO$_2$R |
| $\overset{O}{\underset{\|}{-C-R}}$ |
| $\overset{O}{\underset{\|}{-C-CCl_3}}$ |

TABLE I-continued

| $R_2$ |
|---|
| 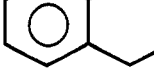 |
| 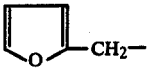 |
| 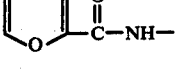 |
| 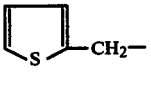 |
|  |
| 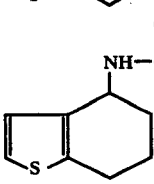 |
| 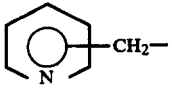 |
|  |
| 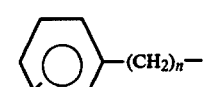 | wherein (in Table I) R is alkyl $C_1$–$C_4$, n is 0, 1 or 2, and Q is selected from the group consisting of the substituents listed in Table II below:

TABLE II

| Q | | |
|---|---|---|
| n = 0 | n = 1 | n = 2 |
| 2-methyl-4-bromo | hydrogen | hydrogen |
| 3,4-methylenedioxy | 4-chloro | |
| 3- or 4-methoxy | 4-methoxy | |
| 4-ethoxy | 3,4-methylenedioxy | |
| 4-chloro | | |
| 4-butoxy | | |
| 2,4-dimethyl | | |
| 2,5-dimethoxy | | |
| 2,4-dichloro | | |
| 4-nitro | | | and $R_1$ and $R_2$ taken together with the associated N(itrogen) is selected from the group consisting of morpholino, piperidino, pyrrolidino, 4-phenylpiperazino, 4-(4-methoxyphenyl)-piperazino, 4-carbethoxypiperazino, 4-oxopiperazino, 1,2,3,4-tetrahydroquinolino and the moiety of the formula:

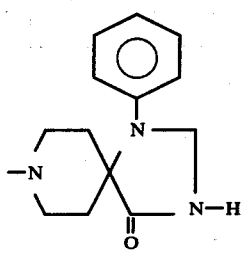

DETAILED DESCRIPTION OF THE INVENTION

A preferred embodiment within the scope of the present invention may be represented by the following formula:

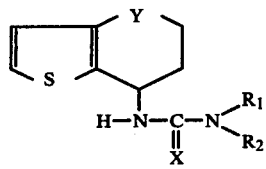  (I)

wherein X, Y, and $R_1$ are as hereinabove defined and $R_2$ is selected from the group consisting of the substituents listed in Table III below:

TABLE III

| $R_2$ |
|---|
| hydrogen |
| alkyl $C_1$–$C_8$ |
| cycloalkyl $C_3$–$C_6$ |
| allyl |
| methallyl |
| 2-butenyl |
| 2-propynyl |
| hydroxy |
| alkoxy $C_1$–$C_6$ |
| allyloxy |
| methallyloxy |
| 2-butenyloxy |
| methoxymethyl |
| phenoxy |
| —$CH_2$—$CH_2$—OH |
| —O—$CH_2$—COOH |
| —$CH_2$—$CH(OR)_2$ |
| —$CH_2$—$CF_3$ |
| —$CH_2$—CN |
| —NH—$CO_2$R |
| $\overset{O}{\underset{\|}{-C}}$—R |
| $\overset{O}{\underset{\|}{-C}}$—$CCl_3$ |

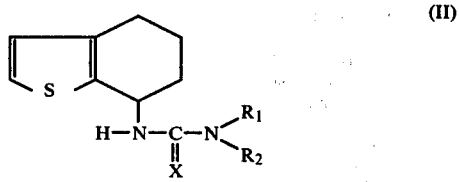

TABLE III-continued

| $R_2$ |
|---|
| benzyloxy (with phenyl–$(CH_2)_n$– and Q substituent) | wherein (in Table III) R and n are as hereinabove defined and Q is selected from the group consisting of the substituents listed in Table IV below:

TABLE IV

| Q | | |
|---|---|---|
| n = 0 | n = 1 | n = 2 |
| 4-chloro | hydrogen | hydrogen |
| 3,4-methylene-dioxy | 4-methoxy | |
| 3- or 4-methoxy | | |
| 4-ethoxy | | |
| 4-butoxy | | |
| 4-methylthio | | |
| 2,4-dimethyl | | |
| 2,4-dichloro | | |
| 4-nitro | | |
| 2-methyl-4-bromo | | |

Another preferred embodiment within the scope of the present invention may be represented by the following formula:

(I)

wherein X, Y and $R_1$ are as hereinabove defined and $R_2$ is selected from the group consisting of the substituents listed in Table V below:

TABLE V

| $R_2$ |
|---|
| hydrogen |
| alkyl $C_1$–$C_8$ |
| cycloalkyl $C_3$–$C_4$ |
| allyl |
| 2-propynyl |
| hydroxy |
| alkoxy $C_1$–$C_6$ |
| methoxymethyl |
| phenoxy |
| 4-methoxyphenyl |
| furfuryl-$CH_2$– |

Another preferred embodiment within the scope of the present invention may be represented by the following formula:

(II)

wherein X is as hereinabove defined and $R_1$ and $R_2$ taken together with the associated N(itrogen) is selected from the group consisting of morpholino, pyrrolidino, 4-phenylpiperazino, 4-(4-methoxyphenyl)piperazino, 1,2,3,4-tetrahydroquinolino and the moiety of the formula:

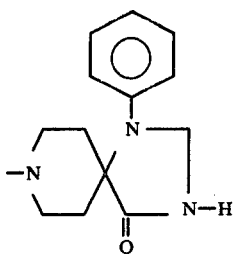

Another preferred embodiment within the scope of the present invention may be represented by the following formula:

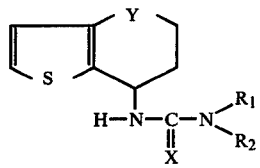

(I)

wherein X and Y are as hereinabove defined, $R_2$ is hydrogen, alkyl $C_1$-$C_4$, allyl, alkoxy $C_1$-$C_4$, 2-propynyl, methoxymethyl or hydroxy and $R_1$ is hydrogen or alkyl $C_1$-$C_4$.

A most preferred embodiment within the scope of the present invention may be represented by the following formula:

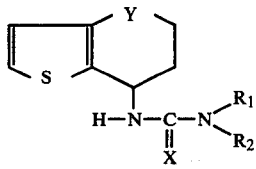

(I)

wherein X and Y are as hereinabove defined, $R_1$ is hydrogen or alkyl $C_1$-$C_4$ and $R_2$ is hydrogen or alkyl $C_1$-$C_4$.

Some of the novel compounds of the present invention (III) may be readily prepared by reacting a 4,5,6,7-tetrahydrobenzo[b]thiophen-7-amine (IV) with an appropriately substituted isocyanate or isothiocyanate (V) as set forth in the following reaction scheme:

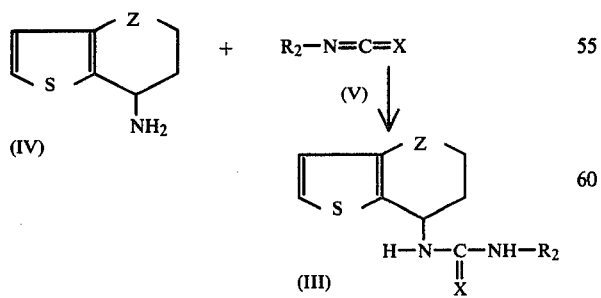

wherein X and $R_2$ are as hereinabove most broadly defined and Z is methylene or carbonyl. The reaction can be carried out using approximately equimolar amounts of the isocyanate or isothiocyanate and the amine or amine acid salt; however, it is generally preferable to employ from 5% to 50% excess of the isocyanate or isothiocyanate. The reaction can be conducted at atmospheric or superatmospheric pressure at a temperature in the range of 0° C. to 100° C., but is preferably conducted at atmospheric pressure at 0° C. to 70° C. in the presence of an organic solvent. Suitable organic solvents include aprotic aromatic solvents such as benzene, toluene, and xylene; chlorinated hydrocarbons such as methylene chloride, chloroform, and dichloroethane; ethers such as tetrahydrofuran, diethyl ether, dimethoxyethane, diethylene glycol dimethyl ether, and dioxane; ketones such as acetone, methyl ethyl ketone, methyl butyl ketone, and methyl isobutyl ketone; or mixtures of said solvents.

When the above reaction is carried out using a 4,5,6,6-tetrahydrobenzo[b]thiophen-7-amine acid salt, it is desirable to add an acid acceptor to the reaction mixture. Suitable acid acceptors include trialkylamines such as triethylamine, trimethylamine, pyridine or the like; alkali metal carbonates such as sodium and potassium carbonate; alkaline earth metal carbonates such as calcium carbonate; strong basic ion exchange resins; and aqueous alkali in a 2-phase system using an immiscible hydrocarbon solvent such as benzene or dichloroethane.

Formula (III) 4,5,6,7-tetrahydroenzo[b]thien-7-yl urea compounds wherein $R_2$ is hydrogen may be advantageously prepared from the above-identified amine (IV) or its acid salts by reacting said amine with an approximately equimolar amount of sodium or potassium cyanate or thiocyanate. However, it is generally preferable to employ 5% to 50% excess of the cyanate or thiocyanate. The reaction can be conducted under the conditions described above in detail. Suitable solvents include water, polar solvents such as $C_1$-$C_3$ alcohols, tetrahydrofuran, dioxane, ethyleneglycol dimethyl ether, diethylene glycol dimethyl ether, acetone, methyl ethyl ketone and the like and mixtures thereof; in the pH range of 5 to 7 and preferably at pH 6.

Certain of the formula (I) 4,5,6,7-tetrahyrobenzo[b]-thien-7-ylurea compounds (VI) may be readily prepared by reacting approximately equimolar amounts of an appropriately substituted 4,5,6,7-tetrahydrobenzo[b]thien-7-yl isocyanate or isothiocyanate (VII) and an appropriately substituted $R_1R_2NH$ amine (VIII) or its acid-addition salt. The reaction can be graphically illustrated as follows:

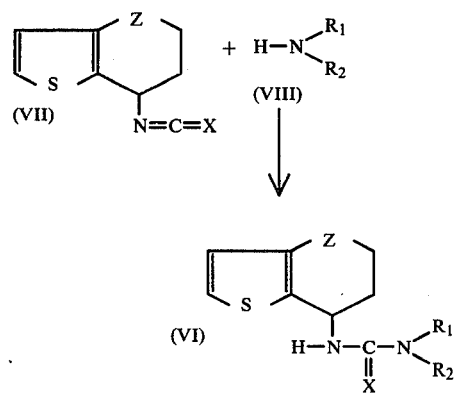

wherein X, Z, R₁ and R₂ are as hereinabove most broadly defined. In practice, the reaction is usually conducted with a slight excess (i.e. up to 20% excess) of the amine in the presence of a solvent, such as described above. Although the reaction may be conducted at superatmospheric pressure and temperatures as high as 100° C., it is generally preferable to conduct the reaction at atmospheric pressure at a temperature between 0° C. to 80° C. When a R₁, R₂NH amine acid salt is used it is most beneficial to introduce into the reaction mixture an acid acceptor such as described above. When an aqueous or a C₁-C₃ alcoholic ammonia or amine solution is used in the above reactive sequence, then the formula (VI) compounds are obtained wherein R₁ and R₂ are both hydrogen.

Preparation of the isocyanates (VII) utilized in the above reaction is readily accomplished by reacting the appropriate 4,5,6,7-tetrahydrobenzo[b]thiophen-7-amines or their acid salts with phosgene, preferably under anhydrous conditions and under a blanket of inert gas such as nitrogen. The reaction is initially carried out at a temperature between about 0° C. to 40° C., preferably 10° C. to 20° C., and then heated to between 50° C. and 100° C., and preferably to from 60° C. to 80° C. The reaction is usually also conducted in the presence of an organic solvent such as benzene, toluene or xylene. The isothiocyanates (VII) can be prepared by reacting the appropriate 4,5,6,7-tetrahydrobenzo[b]thiophen-7-amines with equimolar amounts of carbon disulfide, triethylamine, and a carbodiimide represented by the formula: G—N=C=N—G where G is cyclohexyl, cycloheptyl, alkyl C₄-C₆ or the like. This reaction is generally conducted in the presence of a solvent such as tetrahydrofuran or an ether such as diethyl ether, at a temperature between about −10° C. and +25° C. The product can be isolated by distillation or by dry-column chromatography. Alternatively, the formula (VII) isothiocyanates can be prepared by the reaction of 1,1'-thiocarbonyldiimidazole with 4,5,6,7-tetrahydrobenzo[b]thiophen-7-amines in the presence of chloroform at ambient temperature.

The reaction of thiocarbonyl diimidazole in the above-mentioned reaction may also lead to the isolation of 1-(1-imidazolyl)-3-(4,5,6,7-tetrahydrobenzo[b]thien-7-yl)thiourea. The analogous reaction also occurs when carbonyl diimidazole is used at room temperature and these reactions may be illustrated as follows:

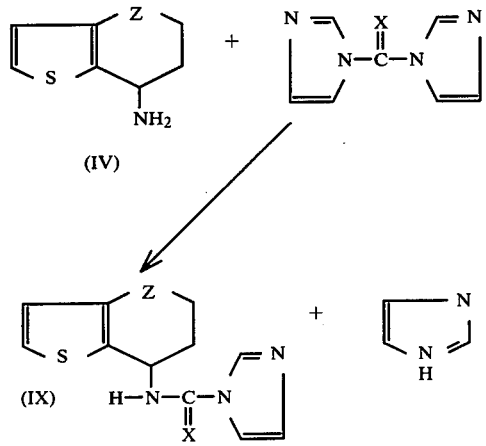

wherein Z and X are as previously defined. This intermediate (IX) has been discovered to be useful for preparing growth promoting urea compounds especially when the corresponding 7-isocyanate or 7-isothiocyanates of the benzothiophene-7-amines are difficult to prepare by conventional methods. The reaction may be illustrated as follows:

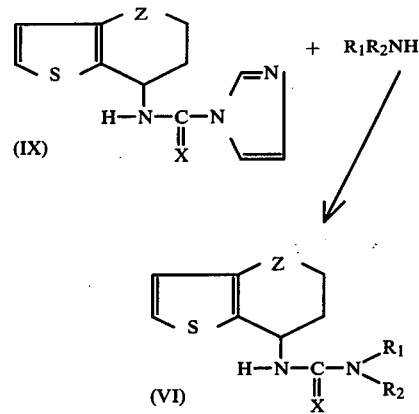

wherein X, Z and R₁ and R₂ are as hereinabove most broadly defined. The reaction is run at room temperature to 100° C. and preferably at 25°-50° C. in inert solvents such as chloroform, tetrahydrofuran, methylene chloride and the like.

The 4-hydroxy analogs of the present invention may be readily prepared from the corresponding formula (X) compounds by reduction with equimolar or excess amount of sodium borohydride as set forth in the following reaction scheme:

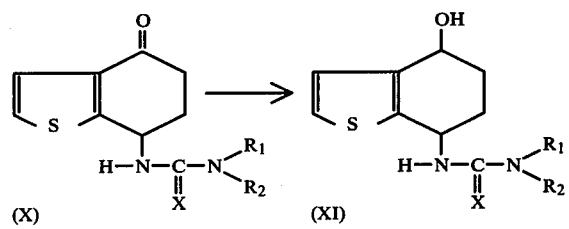

wherein X, R₁ and R₂ are as hereinabove most broadly defined. This reduction is carried out at a temperature range between about 0° C. and 75° C., preferably at 20° C.–40° C., in a lower alkanol solvent such as ethanol, isopropanol, sec-butanol, etc. to afford a mixture of the cis and trans isomers. All of the herein described processes for the preparation of formula (I) 4,5,6,7-tetrahydrobenzo[b]thien-7-ylurea compounds yield racemic (dl) mixtures.

Certain of the novel compounds of the present invention may also be readily prepared by treating an appropriately substituted 4,5,6,7-tetrahydrobenzo[b]thiophen-7-amine (IV) with an appropriately substituted carbamoyl or thiocarbamoyl halide (XII) as set forth in the following reaction scheme:

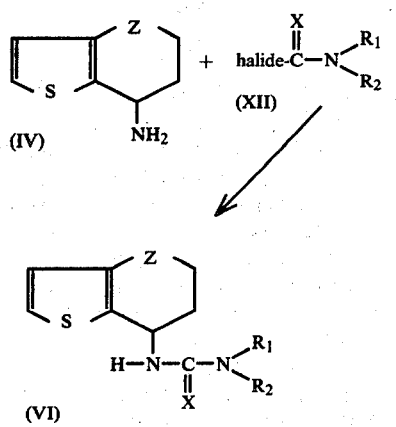

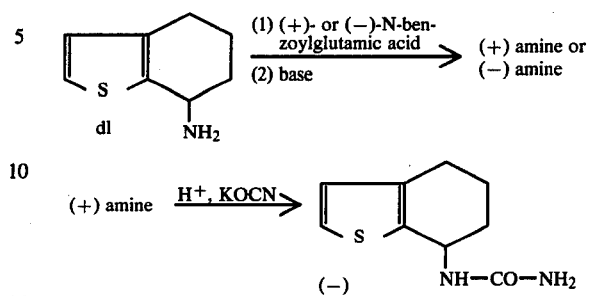

wherein $R_1$, $R_2$, Z and X are as hereinabove most broadly defined and halide may be chloro or bromo with the proviso that $R_2$ may not be hydroxyl, or a group containing hydroxyl, or a thioether. The free base of (IV) may be employed or an acid-addition salt thereof, preferably the hydrochloride, in the presence of an acid acceptor. Suitable acid acceptors may be pyridine, triethylamine (or any suitable tertiary amine), alkali metal carbonates such as potassium carbonate and sodium carbonate, strong basic ion-exchange resins, and aqueous alkali. The reaction may be run from about room temperature up to about 100° C. and preferably at 25° C.-50° C. until the desired reaction is complete. The reaction may be carried out under aqueous conditions or in any inert organic solvent such as tetrahydrofuran, dimethoxyethane, and even alcohols. The carbamoyl chloride or thiocarbamoyl chloride is generally used in equivalent amounts but it may be used in excess.

The preparation of optically active 4,5,6,7-tetrahydrobenzo[b]thiophen-7-amine which is a useful intermediate for the synthesis of certain optically active 4,5,6,7-tetrahydrobenzo[b]thien-7-ylureas of formula (I) may be accomplished as follows. The racemic (dl) 4,5,6,7-tetrahydrobenzo[b]thiophen-7-amine is treated with the (+)-N-benzoylglutamic acid to form a water-insoluble salt of (+)-4,5,6,7-tetrahydrobenzo[b]thiophen-7-amine in high yield. It is not necessary to employ more than one mole of the resolving acid for each two moles of dl amine as a cheaper acid, preferably acetic acid, can be substituted for the balance of the required acid. In this way it is possible to obtain a high yield of the desired (+)-amine based on the resolving acid. The resolved salt, (+)-4,5,6,7-tetrahydrobenzo[b]thiophen-7-amine•(+)-N-benzoylglutamic acid, is treated with alkali which liberates the (+)-amine which separates as an insoluble phase. It can be mechanically separated from the aqueous phase or extracted conventionally with a suitable solvent.

The (−)-amine which remains in solution is then recovered and treated with (−)-N-benzoylglutamic acid and acetic acid in the above-mentioned manner with the molarity adjusted to the amount of (+) amine obtained from the initial resolution. The salt, (−)-4,5,6,7-tetrahydrobenzo[b]thiophen-7-amine•(−)-N-benzoylglutamic acid, crystallizes and is then treated in the above-mentioned manner to give the (−)-amine. With respect to optical isomers, the most preferred optically active ureido compounds for enhancement of growth in animals are those which are derived from the (+)-4,5,6,7-tetrahydrobenzo[b]thiophen-7-amine. Thus, the following reaction scheme will exemplify the sequence in the preparation of the optically active compounds.

The separation of the cis and trans-(−)-4,5,6,7-tetrahydro-4-hydroxybenzo[b]thien-7-ylureas is readily achieved by using preparative high-pressure liquid chromatography on silica gel with 1800 ml. of hexane/1000 ml. of $CHCl_3$/425 ml. of MeOH at a flowrate of 40 ml./minute. Since the configurations have not been established, the isomers are designated as Isomer A and Isomer B. Conversely, if (−)-4,5,6,7-tetrahydrobenzo[b]thiophen-7-amine is used in the above sequence, the resulting derivatives of the opposite sign are obtained.

Because 4,5,6,7-tetrahydro-4-oxobenzo[b]thiophen-7-amine is also a useful intermediate, this compound in its optically active form is desirable. Thus, dl-4,5,6,7-tetrahydro-4-oxobenzo[b]thiophen-7-amine is readily resolved with (+)-tartaric acid in methanol as follows:

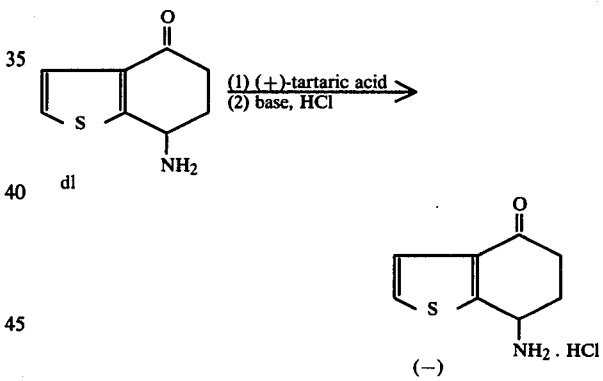

and the resulting crystalline tartrate salt is recrystallized from 95% ethanol. The salt is decomposed with aqueous NaOH solution and the optically active keto-amine is separated by conventional extraction and acidified with HCl to afford (−)-4,5,6,7-tetrahydro-4-oxobenzo[b]thiophen-7-amine hydrochloride, which can be used in the manner described above.

The compounds of this invention are useful as growth-promoting agents for animals such as poultry, fur-bearing and farm animals, and the use of said compounds for this purpose provides the added advantage of improving feed conversion for said animals. As used herein, the term "feed conversion" means the ratio of unit weight of feed per unit weight of gain and improvement in feed conversion means increased weight gain from a given unit of feed consumed.

In practice, a growth-promoting amount of a formula (I) 4,5,6,7-tetrahydrobenzo[b]thien-7-ylurea or an optically active isomer is administered to a host animal usually in, or with, the animal's feed. However, said compound may also be administered as a subcutaneous implant under the skin of said animal or as a parenteral injection. When administered in the feed of chickens, turkeys, sheep, cattle, goats, and the like usually about 0.0001% to 0.08% by weight, and preferably 0.001% to 0.04% by weight of the formula (I) urea, is effective for increasing growth rate and improving feed conversion. When administered to said animals as a parenteral injection or subcutaneous implant, usually in amounts that will supply about 0.001 mg. to 0.20 mg. and preferably 0.005 mg. to 0.10 mg. per kg. of body weight per day of the active compound, they will produce the desired improvement in weight gain and enhance food conversion. In tests with day-old chicks, it is found that 1 ppm to 19 ppm of a 4,5,6,7-tetrahydrobenzo[b]thien-7-ylurea should be administered in the chick feed to produce the desired improvement in weight gain over untreated controls, and likewise to produce improvement in feed conversion.

The compounds of this invention are also useful as herbicidal agents. They are effective for controlling undesirable broadleaf and grass weeds when applied to soil containing seeds of said undesirable weeds, or when applied to the foliage of such plants. Usually about 5 pounds to 15 pounds, and preferably about 8 pounds to 10 pounds, per acre of the active compound is sufficient to provide control of the undesirable plants.

The present invention is further illustrated by the preparation of representative examples set forth below, as well as testing data on typical compounds of the invention.

EXAMPLE 1

Preparation of 1-methyl-3-(4,5,6,7-tetrahydrobenzo[b]thien-7-ylurea 4,5-Dihydro-6H-benzo[b]thiophen-7-one is prepared by the method of MacDowell and Greenwood, Journal of Heterocyclic Chemistry 2, 44 (1965). This ketone is converted to 7-formylamino-4,5,6,7-tetrahydrobenzo[b]thiophen by the method described by Kloetzel et al., Journal of Organic Chemistry 18, 1511 (1953). Hydrolysis of this formamido derivative is accomplished by refluxing for an hour in 1N hydrochloric acid and evaporating to dryness to afford 4,5,6,7-tetrahydrobenzo[b]thiophen-7-amine hydrochloride, m.p. 209°–212° C. A mixture of 50 grams of the amine hydrochloride salt in 100 ml. of water stirred at about 15° C. and a solution if 23.1 grams of potassium cyanate in 100 ml. of water is added dropwise. After completion of the addition, the mixture is warmed slowly to 70° C.–75° C. and held there for an hour. The mixture is cooled and the white solid is collected by filtration and washed with water. The solid is air dried, pulverized, and washed with acetonitrile. Upon drying, this product is treated with hot acetone to afford 4,5,6,7-tetrahydrobenzo[b]thien-7-ylurea, m.p. 211°–213° C.

A mixture of 1.89 grams of the amine salt in 20 ml. of dry tetrahydrofuran is stirred while 1.05 grams of triethylamine and 0.7 ml. of methyl isocyanate are added successively. The mixture is kept at 45° C. for one hour and, after cooling to room temperature, the solid is collected and washed with benzene. On drying, this gives 1-methyl-3-(4,5,6,7-tetrahydrobenzo[b]thien-7-yl)urea, m.p. 192°–195° C.

EXAMPLE 2

Mouse Growth Regulant Tests

CFI female mice from Carworth Farms are received when they are six weeks old. They are housed ten to a cage in air-conditioned rooms (72° F. to 76° F.) with automatically controlled lights, 14 hours on and 10 hours off. The basal diet used in these studies is Purina Laboratory Chow (see description below), which is supplied ad libitum. Water is also allowed ad libitum.

Thirteen days after arrival, the mice are weighed in groups of ten and assigned at random to the different treatments. The concentration of the different compounds in the diet is indicated in the following tables. Twelve days later the mice are weighed again and the experiment terminated. At least three cages (30 mice) of untreated controls are included in each test. Test data are provided in Table VI below wherein data are reported as percent weight gain over controls. Unless otherwise indicated in this table, all compounds tested were dl-racemic mixtures. The following is a description of the diet to which the growth promoting compounds were added.

| DIET | |
|---|---|
| GUARANTEED ANALYSIS | |
| Crude protein not less than | 23.0% |
| Crude fat not less than | 4.5% |
| Crude fiber not more than | 6.0% |
| Ash not more than | 9.0% |

| INGREDIENTS |
|---|
| Meat and bone meal, dried skimmed milk, wheat germ meal, fish meal, animal liver meal, dried beet pulp, ground extruded corn, ground oat groats, soybean meal, dehydrated alfalfa meal, cane molasses, animal fat preserved with BHA, vitamin $B_{12}$ supplement, calcium pantothenate, choline chloride, folic acid, riboflavin supplement, brewers' dried yeast, thiamin, niacin, vitamin A supplement, D activated plant sterol, vitamin E supplement, calcium carbonate, dicalcium phosphate, iodized salt, ferric ammonium citrate, iron oxide, manganous oxide, cobalt carbonate, copper oxide, zinc oxide. |

TABLE VI

Effectiveness of 4,5,6,7-Tetrahydrobenzo[b]thien-7-ylureas as Animal Growth Promoting Agents Reported as Percent Weight Gain Over Controls Using Mice as the Test Animal

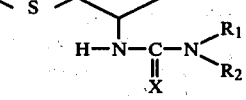

| Rate ppm in Diet | X | Y | $R_1$ | $R_2$ | % Weight Gain Over Controls |
|---|---|---|---|---|---|
| 400 | O | —$CH_2$— | H | H | 53 |
| 400 | O | —$CH_2$— | H | —$CH_3$ | 18 |
| 400 | O | C=O | H | H | 34.5 |

EXAMPLE 3

Herbicidal Activity

The preemergence herbicidal activity of the compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 11.2 kg per hectare of test compound per cup. The treated cups are then placed on greenhouse benches, watered and cared for in accordance with conventional greenhouse procedures. About four weeks after treatment, the tests are terminated and each cup is examined and rated according to the rating system set forth below. The herbicidal proficiency of the active ingredients of the present invention is evident from the test results which are reported in Table VII below.

| Rating System: | % Difference in Growth from the Check* |
|---|---|
| 0 - No effect | 0 |
| 1 - Possible effect | 1–10 |
| 2 - Slight effect | 11–25 |
| 3 - Moderate effect | 26–40 |
| 5 - Definite injury | 41–60 |
| 6 - Herbicidal effect | 61–75 |
| 7 - Good herbicidal effect | 76–90 |
| 8 - Approaching complete kill | 91–99 |
| 9 - Complete kill | 100 |
| 4 - Abnormal growth, that is, a definite physiological malformation but with an over-all effect less than a 5 on the rating scale. | |

*Based on visual determination of stand, size, vigor, chlorosis, growth malformation and over-all plant appearance.

Plant Abbreviations

SE—Sesbania (*Sesbania exaltata*)
LA—Lambsquarters (*Chenopodium album*)
MU—Mustard (*Brassica kaber*)
PI—Pigweed (*Amaranthus retroflexus*)
RW—Ragweed (*Ambrosia artemisiifolia*)
MG—Morningglory (*Ipomoea purpurea*)
BA—Barnyardgrass (*Echinochloa crusgalli*)
CR—Crabgrass (*Digitaria sanguinalis*)
FO—Green foxtail (*Setaria viridis*)
WO—Wild oats (*Avena fatua*)
TW—Teaweed (*Sida spinosa*)
VL—Velvetleaf (*Abutilon theophrasti*)

Table VIII below afford the ureas set forth in Table VIII below:

TABLE VIII

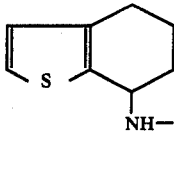

| X | $R_1$ |
|---|---|
| O | isopropyl |
| S | methyl |
| S | n-butyl |
| O | sec-butyl |
| S | allyl |
| O | benzyl |

EXAMPLE 5

Preparation of
1-methoxy-3-(4,5,6,7-tetrahydrobenzo-[b]thien-7-yl)urea

A mixture of methoxyamine hydrochloride (5 g.) in 60 ml. of methylene chloride is stirred and 6 g. of triethylamine in 15 ml. of methylene chloride is added slowly. After half an hour of stirring, 5.4 g. of 4,5,6,7-tetrahydrobenzo[b]thien-7-yl isocyanate is added dropwise. The mixture is stirred at room temperature for an hour and filtered. The filter cake is washed with water and dried to afford the title compound.

Similarly, substitution of amines $R_1R_2NH$ or their hydrochloride salts for methoxyamine hydrochloride affords the ureas set forth in Table IX below wherein $R_1$ and $R_2$ are as defined therein.

TABLE IX

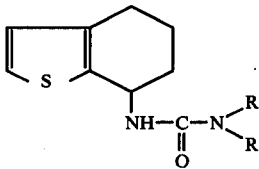

| $R_1$ | $R_2$ |
|---|---|

TABLE VII

| | | Preemergence Herbicidal Activity | | | | | | | | | | | |
|---|---|---|---|---|---|---|---|---|---|---|---|---|---|
| | Rate | | | | | Plant Species | | | | | | | |
| Compound | kg/ha | SE | LA | MU | PI | RW | MG | BA | CR | FO | WO | TW | VL |
| 4,5,6,7-tetrahydrobenzo[b]thien-7-ylurea | 11.2 | 0 | — | 7 | 0 | 0 | 0 | 0 | 7 | 3 | 1 | 2 | 0 |
| 1-methyl-3-(4,5,6,7-tetrahydrobenzo[b]- thien-7-yl)urea | 11.2 | 9 | — | 9 | 9 | 9 | 9 | 7 | 8 | 7 | 6 | 9 | 9 |
| | 10.0 | 9 | — | 9 | 9 | 9 | 9 | 8 | 8 | 8 | — | 9 | 9 |
| | 3.4 | 8 | — | 1 | 6 | 5 | 5 | 3 | 5 | 3 | — | 2 | 2 |

EXAMPLE 4

Preparation of
1-ethyl-3-(4,5,6,7-tetrahydrobenzo[b]thien-7-yl)urea

Equivalent amounts of 4,5,6,7-tetrahydrobenzo[b]thiophen-7-amine hydrochloride, triethylamine, and ethyl isocyanate in methylene chloride are stirred at room temperature for an hour and then heated to reflux for half an hour. The product is collected, washed well with water, and dried to afford the title compound.

Similarly, replacement of ethyl isocyanate with isocyanates $R_1NCX$ where $R_1$ and X are as defined in

| methyl | methyl |
|---|---|
| n-butyl | n-butyl |
| H | n-butoxy |
| H | ethoxy |
| H | benzyloxy |
| H | phenoxy |
| H | allyl |
| H | propargyl |
| methyl | methoxy |
| H | hydroxy |
| methyl | hydroxy |
| H | H |

EXAMPLE 6

Preparation of 4,5,6,7-tetrahydrobenzo[b]thien-7-yl isocyanate

A six gram sample of 4,5,6,7-tetrahydrobenzo[b]thiophen-7-amine is stirred in 20 ml. of toluene at 100° C. and phosgene is slowly introduced into the mixture through a gas tube. The flow of phosgene is terminated after most of the solid amine hydrochloride disappears. The mixture is then filtered and the filtrate is evaporated to dryness to afford the title compound.

EXAMPLE 7

Preparation of 4,5,6,7-tetrahydrobenzo[b]thien-7-yl isothiocyanate

A 38 g. sample of 4,5,6,7-tetrahydrobenzo[b]thiophen-7-amine, which is obtained by neutralizing the amine hydrochloride with 10% NaOH, is stirred in 500 ml. of ethyl acetate under nitrogen atmosphere and 25.4 g. of triethylamine is added. Subsequently, 21 g. of carbon disulfide is added and then 52 g. of dicyclohexylcarbodiimide is added. The mixture is stirred for 18 hours at room temperature and heated to 50° C. for two hours. The mixture is cooled, filtered, the filter cake is washed with ethyl acetate and the filtrate is evaporated to dryness in vacuo. The residue is then stirred in diethyl ether and the ether solution is filtered and evaporated to dryness to afford the crude title compound.

EXAMPLE 8

Preparation of 1-methyl-1-methoxy-3-(4,5,6,7-tetrahydrobenzo[b]thien-7-yl)thiourea In the manner described in Example 5, 4,5,6,7-tetrahydrobenzo[b]thien-7-yl isothiocyanate is allowed to react with O,N-dimethylhydroxylamine hydrochloride to afford the title compound.

Similarly, substitution of amines $R_1R_2NH$ for O,N-dimethylhydroxylamine hydrochloride in the above-mentioned procedure affords the thioureas set forth in Table X below.

TABLE X

| $R_1$ | $R_2$ |
|---|---|
| H | H |
| H | n-butyl |
| H | isopropyl |
| methyl | methyl |
| H | phenoxy |
| H | benzyloxy |
| H | propargyl |
| H | allyl |
| H | n-butoxy |
| n-butyl | n-butyl |
| methyl | hydroxy |

EXAMPLE 9

Preparation of 1-methoxymethyl-3-(4,5,6,7-tetrahydrobenzo[b]thien-7-yl)urea

A sample of 4,5,6,7-tetrahydrobenzo[b]thien-7-ylurea (8 grams) in 150 ml. of methanol is stirred and 2.1 grams of sodium hydroxide pellets and 2.3 grams of paraformaldehyde in 50 ml of methanol are added. The mixture is stirred, heated at reflux and cooled after 8 hours. The mixture is evaporated to dryness in vacuo and the residue is collected and washed with water to afford the title compound.

EXAMPLE 10

Preparation of 4-(2-thienyl)-4-oxobutyric acid oxime

A mixture of 22.6 g. of hydroxylamine hydrochloride and 26 g. of NaOH in 300 ml. of water is stirred and 30 g. of 4-(2-thienyl)-4-oxobutyric acid is added to afford a clear yellow solution. The mixture is stirred for two hours at room temperature and acidified with 3N HCl to pH 2 to give a white precipitate. After stirring an additional half hour, the mixture is cooled in ice and filtered. The filter cake is washed with water and dried to afford the title compound, m.p. 133°–138° C.

EXAMPLE 11

Preparation of 4-amino-4-(2-thienyl)butyric acid

Heavy-duty aluminum foil is cut into ½-inch squares and 20 g. of this material is slurried in hexane and decanted. The foil is heated on a steam bath to dry and then stirred in 400 ml. of aqueous 2% $HgCl_2$ for about 13 seconds. The mixture is quickly filtered and rinsed with 300 ml. of absolute ethanol and then with 300 ml. of diethyl ether. The amalgam is added to a stirred mixture containing 10 g. of 4-(2-thienyl)-4-oxobutyric acid oxime in 150 ml. of water. The temperature is allowed to rise to reflux temperature from the reaction exotherm and after 20 minutes the mixture is cooled to room temperature. After stirring for 16 hours, the mixture is filtered and the filter cake is washed with 150 ml. of water. The filtrate is evaporated to dryness in vacuo and the residue is stirred with 150 ml. of acetone and filtered to give 3 g. of the title compound, m.p. 148°–156° C.

EXAMPLE 12

Preparation of 4-phthalimido-4-(2-thienyl)butyric acid

A mixture containing one gram of 4-amino-4-(2-thienyl)butyric acid and 0.8 g. of phthalic anhydride in 25 ml. of xylene containing 0.55 g. of triethylamine is heated to reflux the water is removed by azeotroping. After 1.5 hours the mixture is cooled and stirred overnight at room temperature. It is then evaporated to dryness to afford the title compound as a glassy material.

EXAMPLE 13

Preparation of N-(4,5,6,7-tetrahydro-4-oxobenzo[b]thien-7-yl)phthalimide

A 1.05 g. sample of 4-phthalimido-4-(2-thienyl)butyric acid is added to 5 ml. of liquid hydrogen fluoride in a polyethylene tube at ice bath temperature. The mixture is stirred to give a solution and after 10 minutes the solution is warmed to distill the hydrogen fluoride.

The gummy residue is stirred in 20 ml. of water, the mixture is made alkaline (pH 10–11) with 3N NaOH and cooled in ice. The aqueous layer is decanted and the semisolid is triturated with 20 ml. of diethyl ether. The title product is then collected and dried to give 0.59 g., m.p. 150°–157° C.

The title compound is also obtained by cyclization of 4-phthalimido-4-(2-thienyl)butyric acid chloride in $CH_2Cl_2$ at 15° C. in the presence of 2 equivalents of $SnCl_4$. After the reaction is completed, the reaction mixture is poured into water and the organic layer is separated. Evaporation of the organic layer affords the crude title compound. The acid chloride is prepared by stirring the butyric acid with an equivalent of $SOCl_2$ or $COCl_2$ in benzene at 10°–15° C. until the reaction is complete. Evaporation of the reaction mixture to dryness in vacuo affords the 4-phthalimido-4-(2-thienyl)-butyric acid chloride.

EXAMPLE 14

Preparation of 4,5,6,7-tetrahydro-4-oxobenzo[b]thiophen-7-amine

A 0.55 g. sample of N-(4,5,6,7-tetrahydro-4-oxobenzo[b]thien-7-yl)phthalimide is stirred and heated at reflux with 5 ml. of 6N HCl and one ml. of ethanol for 16 hours. Subsequently, the ethanol is distilled off and refluxing is continued for another 4 hours with the addition of 2 ml. of concentrated HCl. The mixture is cooled in ice, the white crystals of phthalic acid are filtered and washed with 5 ml. of water. The filtrate is washed with 15 ml. of $CHCl_3$ and the aqueous solution of 4,5,6,7-tetrahydro-4-oxobenzo[b]thiophen-7-amine hydrochloride is neutralized until the solution is at pH 10–11 with 50% aqueous NaOH. The amine is then extracted from the aqueous mixture with chloroform (3×25 ml.). The combined extracts are dried over $MgSO_4$ and evaporated to afford 0.17 g. of light yellow syrup. This gives the title compound with infrared absorption bands at 1660, 1620 and 1520 $cm^{-1}$.

EXAMPLE 15

Preparation of dl-4,5,6,7-tetrahydro-4-oxobenzo[b]thien-7-ylurea

A 0.17 g. sample of dl-4,5,6,7-tetrahydro-4-oxobenzo[b]thiophen-7-amine is stirred in 10 ml. of water, acidified with 3N HCl to pH 3–4, and 0.3 g. of KOCN is added. The mixture is stirred at room temperature for 16 hours, and the title compound is collected by filtration, washed with water and dried. It melts at 238°–242° C. and recrystallization from methanol gives analytical sample of the title compound, m.p. 240°–241° C.

Replacement of the above amine by (+)- or (−)-4,5,6,7-tetrahydro-4-oxobenzo[b]thiophen-7-amine, which is obtained by resolving dl-4,5,6,7-tetrahydro-4-oxobenzo[b]thiophen-7-amine with (+) tartaric acid or (−) tartaric acid, respectively, in methanol followed by recrystallization and neutralization of the 4,5,6,7-tetrahydro-4-oxobenzo[b]thiophen-7-amine.tartaric acid salt with 10% NaOH solution affords the optically active title compounds.

EXAMPLE 16

Preparation of 1-methyl-3-(4,5,6,7-tetrahydro-4-oxobenzo[b]thien-7-ylurea

In nitrogen atmosphere, equivalent quantities of methyl isocyanate and 4,5,6,7-tetrahydro-4-oxobenzo[b]thiophen-7-amine are allowed to react in $CH_2Cl_2$. After stirring for several hours, the title compound is collected.

Similarly, replacement of methyl isocyanate with $R_2NCX$, wherein X and $R_2$ are as defined in Table XI below, affords ureas of the following structure:

TABLE XI

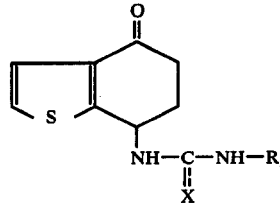

| X | $R_2$ |
|---|---|
| S | methyl |
| O | ethyl |
| S | ethyl |
| O | n-propyl |
| O | isopropyl |
| S | n-propyl |
| O | n-butyl |
| O | sec-butyl |
| S | n-butyl |
| O | benzyl |
| S | benzyl |
| S | allyl |

EXAMPLE 17

Preparation of 1-(2-propynyl)-3-(4,5,6,7-tetrahydro-4-oxobenzo[b]thien-7-ylurea

Equivalent quantities of 4,5,6,7-tetrahydro-4-oxobenzo[b]thiophen-7-amine and carbonyl diimidazole are allowed to react in $CH_2Cl_2$ by adding the amine in $CH_2Cl_2$ to the imidazole in $CH_2Cl_2$. After several hours of stirring, an equivalent amount of 2-propargyl amine is added and stirring is continued until the reaction is complete by thin-layer chromatographic analysis. The title compound is then collected.

Similarly, replacement of propargyl amine with $R_1R_2NH$ amines affords ureas of the following structure, wherein $R_1$ and $R_2$ are as defined in Table XII below:

TABLE XII

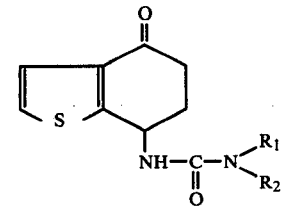

| $R_1$ | $R_2$ |
|---|---|
| H | ethyl |
| methyl | methyl |
| n-butyl | n-butyl |
| methyl | methoxy |
| H | methoxy |
| H | ethoxy |
| H | n-butoxy |
| H | phenoxy |
| H | benzyloxy |
| H | n-butyl |
| H | isopropyl |

Substitution of carbonyl diimidazole with thiocarbonyl diimidazole in the abovementioned reactions affords the corresponding thioureas of the above structure wherein the ureido moiety is now replaced by a thioureido group.

EXAMPLE 18

Preparation of cis- and trans-4,5,6,7-tetrahydro-4-hydroxybenzo[b]thien-7-ylurea.

A one mole sample of 4,5,6,7-tetrahydro-4-oxobenzo[b]thien-7-ylurea is stirred in ethanol and 1.6 moles of NaBH$_4$ is added. The mixture is stirred overnight at room temperature and water is added. After stirring for an hour, the mixture is evaporated to near-dryness (until ethanol is distilled) in vacuo and acetic acid is added until foaming ceases. The mixture is stirred for an hour and the title compound is collected by filtration. The mother liquor is evaporated to dryness and the residue is extracted with hot acetone several times. Removal of the acetone affords additional title compound. Separation of the cis and trans isomers is possible by using high pressure liquid chromatography on silica gel with hexane/CHCl$_3$/methanol. Substitution of (+) and (−) tetrahydro-4-oxobenzo[b]thien-7-ylurea for the above dl urea in the above-mentioned reduction affords the (+) and (−) tetrahydro-4-hydroxybenzo[b]thien-7-ylureas, cis/trans.

Similarly, substitution of 4,5,6,7-tetrahydro-4-oxobenzo[b]thien-7-ylurea with ureas of structure (XII) afford ureas of structure (XIII) wherein R$_1$ and R$_2$ are as defined in Table XIII below:

TABLE XIII

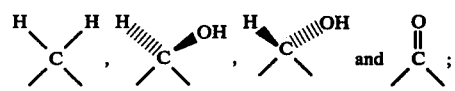

(XII)

(XIII)

| R$_1$ | R$_2$ | X |
|---|---|---|
| CH$_3$ | CH$_3$— | S |
| H | CH$_3$— | S |
| H | CH$_3$— | O |
| CH$_3$ | CH$_3$— | O |
| H | C$_2$H$_5$— | O |
| H | C$_2$H$_5$— | S |
| H | iso-C$_3$H$_7$— | O |
| H | n-C$_4$H$_9$— | S |
| H | n-C$_4$H$_9$— | O |
| H | HC≡C—CH$_2$— | O |
| H | H$_2$C=CH—CH$_2$— | O |
| H | H$_2$C=CH—CH$_2$— | S |
| H | CH$_3$O— | O |
| H | C$_2$H$_5$O— | O |
| H | phenoxy | O |
| H | benzyloxy | O |
| n-C$_4$H$_9$ | n-C$_4$H$_9$— | O |
| H | n-C$_4$H$_9$O— | O |
| H | CH$_3$O— | S |

I claim:
1. A compound selected from the group consisting of those of the formulae:

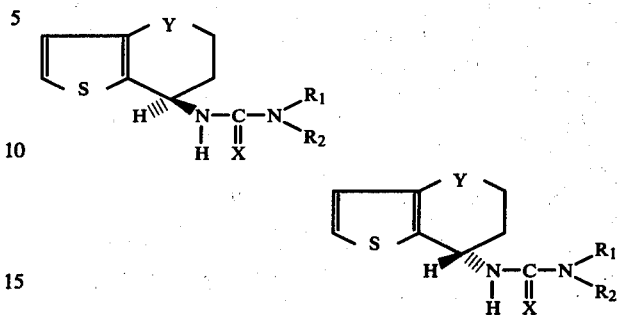

wherein X is oxygen or sulfur; Y is a divalent radical selected from the group consisting of those of the formulae:

$$\diagup_{H}^{H}\diagdown C \diagup_{H}^{H}\diagdown \;,\; \diagup_{H}^{H}\diagdown C \diagup_{OH}\diagdown \;,\; \diagup_{H}^{H}\diagdown C \diagup_{OH}\diagdown \;\; \text{and} \;\; \diagup_{}^{O}\diagdown C \diagdown \;;$$

R$_1$ is selected from the group consisting of hydrogen, alkyl C$_1$–C$_4$, cycloalkyl C$_3$–C$_6$, allyl, 2-propynyl, benzyl and β-phenethyl; R$_2$ is selected from the group consisting of the substituents listed in the following table:

hydrogen
alkyl C$_1$–C$_{12}$
cycloalkyl C$_3$–C$_6$
allyl
methallyl
2-butenyl
2-propynyl
hydroxy
alkoxy C$_1$–C$_6$
allyloxy
methallyloxy
2-butenyloxy
methoxymethyl
phenoxy
—CH$_2$—CH$_2$—OH
—CH$_2$—CH$_2$—O—CH$_3$
—CH$_2$—CH$_2$—S—CH$_3$
—CH$_2$—CH(OR)$_2$
—CH$_2$—CF$_3$
—CH$_2$—CN
—CH$_2$—CO$_2$R
—NH—CO$_2$R $$-\overset{O}{\underset{\|}{C}}-R$$

$$-\overset{O}{\underset{\|}{C}}-CCl_3$$

[thienylmethyl structure]—CH$_2$—

[tetrahydrobenzothienyl structure]

wherein R is alkyl C$_1$–C$_4$, n is 0, 1 or 2, and Q is selected from the group consisting of the substituents listed in the following table:

| n = 0 | n = 1 | n = 2 |
|---|---|---|
| 2-methyl-4-bromo | hydrogen | hydrogen |
|  | 4-chloro |  |
| 3- or 4-methoxy | 4-methoxy |  |
| 4-ethoxy |  |  |
| 4-chloro |  |  |
| 4-butoxy |  |  |
| 4-methylthio |  |  |
| 2,4-dimethyl |  |  |
| 2,4-dichloro |  |  |
| 4-nitro |  |  |

2. A compound according to claim 1 selected from the group consisting of the dextrorotatory enantiomorph, the levorotatory enantiomorph, and the racemic mixture thereof of a compound of the formula:

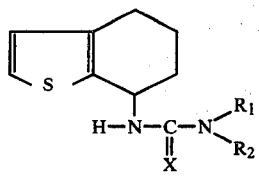

wherein X is oxygen or sulfur; $R_1$ is selected from the group consisting of hydrogen, alkyl $C_1$-$C_4$, cycloalkyl $C_3$-$C_6$, allyl, 2-propynyl, benzyl and $\beta$-phenethyl; $R_2$ is selected from the group consisting of the substituents listed in the following table:

hydrogen
alkyl $C_1$-$C_2$
cycloalkyl $C_3$-$C_6$
allyl
methallyl
2-butenyl
2-propynyl
hydroxy
alkoxy $C_1$-$C_6$
allyloxy
methallyloxy
2-butenyloxy
methoxymethyl
phenoxy
—$CH_2$—$CH_2$—OH
—$CH_2$—$CH_2$—O—$CH_3$
—$CH_2$—$CH_2$—S—$CH_3$
—$CH_2$—$CH(OR)_2$
—$CH_2$—$CF_3$
—$CH_2$—CN
—$CH_2$—$CO_2R$
—NH—$CO_2R$ $$-\overset{O}{\underset{\|}{C}}-R$$

$$-\overset{O}{\underset{\|}{C}}-CCl_3$$

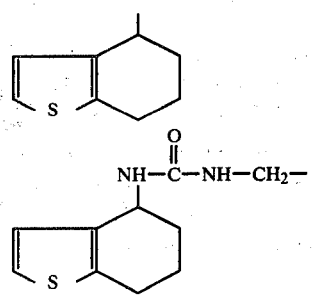

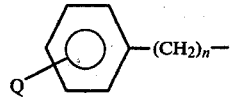

wherein R is alkyl $C_1$-$C_4$, n is 0, 1 or 2, and Q is selected from the group consisting of the substituents listed in the following table:

| n = 0 | n = 1 | n = 2 |
|---|---|---|
| 2-methyl-4-bromo | hydrogen | hydrogen |
|  | 4-chloro |  |
| 3- or 4-methoxy | 4-methoxy |  |
| 4-ethoxy |  |  |
| 4-chloro |  |  |
| 4-butoxy |  |  |
| 4-methylthio |  |  |
| 2,4-dimethyl |  |  |
| 2,4-dichloro |  |  |
| 4-nitro |  |  |

3. The racemic mixture according to claim 2 wherein X is oxygen and $R_1$ and $R_2$ are hydrogen; dl-4,5,6,7-tetrahydrobenzo[b]thien-7-ylurea.

4. The racemic mixture according to claim 2 wherein X is oxygen, $R_1$ is hydrogen, and $R_2$ is methyl; dl-1-methyl-3-(4,5,6,7-tetrahydrobenzo[b]thien-7-yl)urea.

5. The dextrorotatory enantiomorph according to claim 2 wherein X is oxygen and $R_1$ and $R_2$ are hydrogen; d-4,5,6,7-tetrahydrobenzo[b]thien-7-ylurea.

6. The levorotatory enantiomorph according to claim 2 wherein X is oxygen and $R_1$ and $R_2$ are hydrogen; l-4,5,6,7-tetrahydrobenzo[b]thien-7-ylurea.

7. The racemic mixture according to claim 2 wherein X is oxygen, $R_1$ is hydrogen, and $R_2$ is methoxy; dl-1-methoxy-3-(4,5,6,7-tetrahydrobenzo[b]thien-7-yl)urea.

8. The compound according to claim 1 selected from the group consisting of the dextrorotatory enantiomorph, the levorotatory enantiomorph, and the racemic mixture thereof of a compound of the formula:

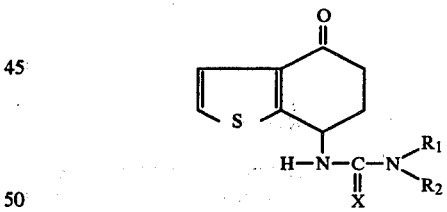

wherein X is oxygen or sulfur; $R_1$ is selected from the group consisting of hydrogen, alkyl $C_1$-$C_4$, cycloalkyl $C_3$-$C_6$, allyl, 2-propynyl, benzyl and $\beta$-phenethyl; $R_2$ is selected from the group consisting of the substituents listed in the following table:

hydrogen
alkyl $C_1$-$C_{12}$
cycloalkyl $C_3$-$C_6$
allyl
methallyl
2-butenyl
2-propynyl
hydroxy
alkoxy $C_1$-$C_6$
allyloxy
methallyloxy
2-butenyloxy
methoxymethyl phenoxy
—CH₂—CH₂—OH
—CH₂—CH₂—O—O—CH₃
—CH₂—CH₂—S—CH₃
—CH₂—CH(OR)₂
—CH₂—CF₃
—CH₂—CN
—CH₂—CO₂R
—NH—CO₂R $$-\overset{O}{\underset{\|}{C}}-R$$

$$-\overset{O}{\underset{\|}{C}}-CCl_3$$

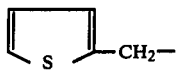

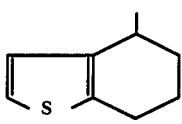

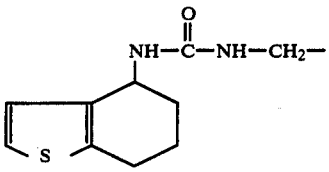

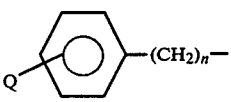

wherein R is alkyl $C_1$-$C_4$, n is 0, 1 or 2, and Q is selected from the group consisting of the substituents listed in the following table:

| n = 0 | n = 1 | n = 2 |
| --- | --- | --- |
| 2-methyl-4-bromo | hydrogen | hydrogen |
|  | 4-chloro |  |
| 3- or 4-methoxy | 4-methoxy |  |
| 4-ethoxy |  |  |
| 4-chloro |  |  |
| 4-butoxy |  |  |
| 4-methylthio |  |  |
| 2,4-dimethyl |  |  |
| 2,4-dichloro |  |  |
| 4-nitro |  |  |

9. The racemic mixture according to claim 8 wherein X is oxygen and R₁ and R₂ are hydrogen; dl-4,5,6,7-tetrahydro-4-oxobenzo[b]thien-7-ylurea.

10. The racemic mixture according to claim 8 wherein X is oxygen, R₁ is hydrogen, and R₂ is methyl; dl-1-methyl-3-(4,5,6,7-tetrahydro-4-oxobenzo[b]thien-7-yl)urea.

11. The dextrorotatory enantiomorph according to claim 8 wherein X is oxygen and R₁ and R₂ are hydrogen; d-4,5,6,7-tetrahydro-4-oxobenzo[b]thien-7-ylurea.

12. The levorotatory enantiomorph according to claim 8 wherein X is oxygen and R₁ and R₂ are hydrogen; l-4,5,6,7-tetrahydro-4-oxobenzo[b]thien-7-ylurea.

13. The compound according to claim 1 selected from the group consisting of the cis-dextrorotatory enantiomorph, the cis-levorotatory enantiomorph, the racemic mixture of the cis-enantiomorphs, the trans-dextrorotatory enantiomorph, the trans-levorotatory enantiomorph, and the racemic mixture of the trans-enantiomorphs of a compound of the formula:

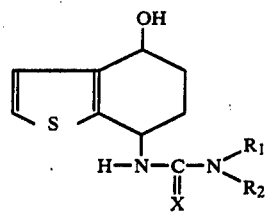

wherein X is oxygen or sulfur; R₁ is selected from the group consisting of hydrogen, alkyl $C_1$-$C_4$, cycloalkyl $C_3$-$C_6$, allyl, 2-propynyl, benzyl and β-phenethyl; R₂ is selected from the group consisting of the substituents listed in the following table:

hydrogen
alkyl $C_1$-$C_{12}$
cycloalkyl $C_3$-$C_6$
allyl
methyallyl
2-butenyl
2-propynyl
hydroxy
alkoxy $C_1$-$C_6$
allyloxy
methallyloxy
2-butenyloxy
methoxymethyl
phenoxy
—CH₂—CH₂—OH
—CH₂—CH₂—O—CH₃
—CH₂—CH₂—S—CH₃
—CH₂—CH(OR)₂
—CH₂—CF₃
—CH₂—CN
—CH₂—CO₂R
—NH—CO₂R $$-\overset{O}{\underset{\|}{C}}-R$$

$$-\overset{O}{\underset{\|}{C}}-CCl_3$$

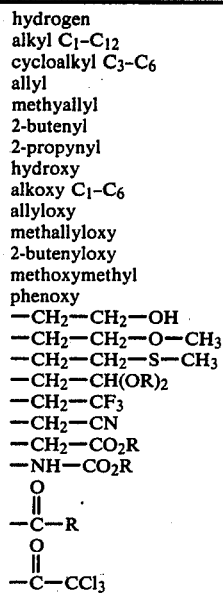

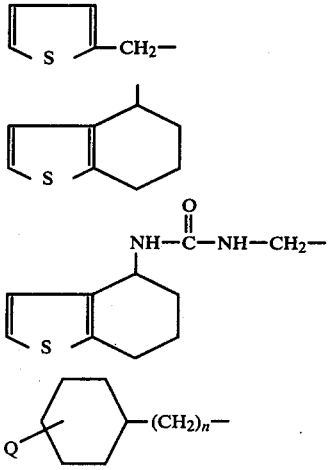

wherein R is alkyl $C_1$-$C_4$, n is 0, 1 or 2, and Q is selected from the group consisting of the substituents listed in the following table:

| n = 0 | n = 1 | n = 2 |
| --- | --- | --- |
| 2-methyl-4-bromo | hydrogen | hydrogen |
|  | 4-chloro |  |
| 3- or 4-methoxy | 4-methoxy |  |
| 4-ethoxy |  |  |
| 4-chloro |  |  |

-continued

| | n = 0 | n = 1 | n = 2 |
|---|---|---|---|
| 4-butoxy | | | |
| 4-methylthio | | | |
| 2,4-dimethyl | | | |
| 2,4-dichloro | | | |
| 4-nitro | | | |

14. The cis-racemic mixture according to claim 13 wherein X is oxygen and $R_1$ and $R_2$ are hydrogen; dl-cis-4,5,6,7-tetrahydro-4-hydroxybenzo[b]thien-7-ylurea.

15. The cis-racemic mixture according to claim 14 wherein X is oxygen, $R_1$ is hydrogen, and $R_2$ is methyl; dl-cis-1-methyl-3-(4,5,6,7-tetrahydro-4-hydroxybenzo[b]thien-7-yl)urea.

16. The trans-racemic mixture according to claim 14 wherein X is oxygen and $R_1$ and $R_2$ are hydrogen; dl-trans-4,5,6,7-tetrahydro-4-hydroxybenzo[b]thien-7-ylurea.

17. The trans-racemic mixture according to claim 14 wherein X is oxygen, $R_1$ is hydrogen, and $R_2$ is methyl; dl-trans-1-methyl-3-(4,5,6,7-tetrahydro-4-hydroxybenzo[b]thien-7-yl)urea.

18. The cis-dextrorotatory enantiomorph according to claim 14 wherein X is oxygen and $R_1$ and $R_2$ are hydrogen; d-cis-4,5,6,7-tetrahydro-4-hydroxybenzo[b]thien-7-ylurea.

19. The cis-levorotatory enantiomorph according to claim 14 wherein X is oxygen and $R_1$ and $R_2$ are hydrogen; l-cis-4,5,6,7-tetrahydro-4-hydroxybenzo[b]thien-7-ylurea.

20. The trans-dextrorotatory enantiomorph according to claim 14 wherein X is oxygen and $R_1$ and $R_2$ are hydrogen; d-trans-4,5,6,7-tetrahydro-4-hydroxybenzo[b]thien-7-ylurea.

21. The trans-levorotatory enantiomorph according to claim 14 wherein X is oxygen and $R_1$ and $R_2$ are hydrogen; l-trans-4,5,6,7-tetrahydro-4-hydroxybenzo[b]thien-7-ylurea.

22. The compound according to claim 1 selected from the group consisting of the dextrorotatory enantiomorph, the levorotatory enantiomorph, and the racemic mixture thereof of a compound of the formula:

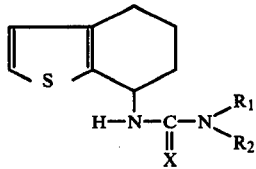

wherein X is oxygen or sulfur; $R_2$ is selected from the group consisting of hydrogen, alkyl $C_1-C_4$, allyl, alkoxy $C_1-C_4$, 2-propynyl, hydroxy and methoxymethyl; and $R_1$ is hydrogen or alkyl $C_1-C_4$.

23. A compound selected from the group consisting of the dextrorotatory enantiomorph, the levorotatory enantiomorph, and the racemic mixture thereof of a compound of the formula:

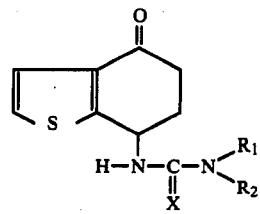

wherein X is oxygen or sulfur; $R_2$ is selected from the group consisting of hydrogen, alkyl $C_1-C_4$, allyl, alkoxy $C_1-C_4$, 2-propynyl, hydroxy and methoxymethyl; and $R_1$ is hydrogen or alkyl $C_1-C_4$.

24. The compound according to claim 1 selected from the group consisting of the cis-dextrorotatory enantiomorph, the cis-levorotatory enantiomorph, the racemic mixture of the cis-enantiomorphs, the trans-dextrorotatory enantiomorph, the trans-levorotatory enantiomorph, and the racemic mixture of the trans-enantiomorphs of a compound of the formula:

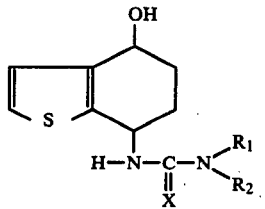

wherein X is oxygen or sulfur; $R_2$ is selected from the group consisting of hydrogen, alkyl $C_1-C_4$, allyl, alkoxy $C_1-C_4$, 2-propynyl, hydroxy and methoxymethyl; and $R_1$ is hydrogen or alkyl $C_1-C_4$.

25. The compound according to claim 1 having the formula:

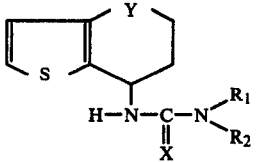

wherein X is oxygen or sulfur; Y is a divalent moiety selected from the group consisting of those of the formulae:

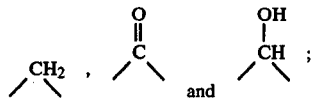

and $R_1$ and $R_2$ are each individually selected from the group consisting of hydrogen and alkyl having from one to four carbon atoms.

* * * * *